United States Patent
Burbar et al.

(10) Patent No.: US 12,295,768 B2
(45) Date of Patent: May 13, 2025

(54) COOLING SYSTEM INTEGRATED WITHIN MODULAR, DETECTOR ELECTRONIC ASSEMBLY FOR A DIAGNOSTIC MEDICAL IMAGING APPARATUS

(71) Applicant: Siemens Medical Solutions USA, Inc., Malvern, PA (US)

(72) Inventors: Ziad Burbar, Knoxville, TN (US); John Keller, Knoxville, TN (US); Andrew Philip Moor, Knoxville, TN (US); James L. Corbeil, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 401 days.

(21) Appl. No.: 17/998,163

(22) PCT Filed: Jun. 23, 2021

(86) PCT No.: PCT/US2021/070752
§ 371 (c)(1),
(2) Date: Nov. 8, 2022

(87) PCT Pub. No.: WO2021/263275
PCT Pub. Date: Dec. 30, 2021

(65) Prior Publication Data
US 2023/0218253 A1 Jul. 13, 2023

Related U.S. Application Data

(63) Continuation-in-part of application No. PCT/US2020/070462, filed on Aug. 26, 2020, and a
(Continued)

(51) Int. Cl.
*A61B 6/00* (2024.01)
*A61B 6/03* (2006.01)

(52) U.S. Cl.
CPC ............ *A61B 6/4488* (2013.01); *A61B 6/035* (2013.01)

(58) Field of Classification Search
CPC ....... A61B 6/4488; A61B 6/035; A61B 6/037; A61B 6/4266; A61B 6/4411; A61B 6/4417; H01L 23/34
See application file for complete search history.

(56) References Cited

U.S. PATENT DOCUMENTS 8,018,717 B2 * 9/2011 Corbeil ................. G01T 1/1603
174/15.1
8,581,196 B2 11/2013 Yamaya et al.
(Continued)

FOREIGN PATENT DOCUMENTS

CN 210130852 3/2020

OTHER PUBLICATIONS

International Search Report for Corresponding PCT Appln No. PCT/US2020/070462, mailed Jun. 1, 2021.
(Continued)

*Primary Examiner* — David J Makiya
*Assistant Examiner* — Soorena Kefayati

(57) ABSTRACT

A fluid coolant system for a gantry of a medical imaging apparatus cools scalable detector electronic assemblies (DEAs) within the gantry. Each DEA includes within its modular housing a first chill plate thermally conductively coupled to cooling detector elements therein and a separate, second chill plate thermally conductively coupled to other electronic components therein, such as electronic circuit boards and/or power supplies. In some embodiments, the first chill plate is oriented between the detector elements and the second chill plate, for thermally isolating the detector elements from other heat dissipating components within the DEA. In some embodiments, coolant flow cascades sequen-
(Continued)

tially through the first chill plate and then through the second chill plate.

10 Claims, 8 Drawing Sheets

Related U.S. Application Data continuation-in-part of application No. 16/946,514, filed on Jun. 25, 2020, now Pat. No. 11,154,262.

(60) Provisional application No. 63/198,079, filed on Sep. 28, 2020.

(56) References Cited

U.S. PATENT DOCUMENTS

| | | | |
|---|---|---|---|
| 8,590,331 B2 | 11/2013 | Corbeil et al. | |
| 8,699,660 B2* | 4/2014 | Joshi | G05D 23/1931 378/19 |
| 10,178,976 B2* | 1/2019 | Liu | F28F 1/14 |
| 10,353,084 B1* | 7/2019 | Wagner | A61B 6/037 |
| 2005/0067579 A1 | 3/2005 | Tsuchiya | |
| 2009/0257548 A1* | 10/2009 | Joshi | A61B 6/035 378/4 |
| 2010/0026301 A1* | 2/2010 | Stocker | G01R 33/481 324/318 |
| 2012/0091341 A1* | 4/2012 | Corbeil | F28F 1/16 165/181 |
| 2013/0037251 A1* | 2/2013 | Joshi | G05D 23/1919 378/19 |
| 2013/0284936 A1 | 10/2013 | McBroom et al. | |
| 2014/0153689 A1* | 6/2014 | Anno | A61B 6/4488 29/401.1 |
| 2014/0314197 A1* | 10/2014 | Watanabe | A61B 6/4488 378/4 |
| 2015/0073272 A1 | 3/2015 | Corbeil | |
| 2017/0059720 A1 | 3/2017 | McBroom et al. | |
| 2017/0112454 A1 | 4/2017 | Yun et al. | |
| 2018/0059270 A1 | 3/2018 | Hefetz | |
| 2019/0187308 A1* | 6/2019 | Liu | F25B 41/40 |
| 2022/0249046 A1 | 8/2022 | Sun et al. | |

OTHER PUBLICATIONS

International Search Report for Corresponding PCT Appln No. PCT/US2021/070752, mailed Sep. 10, 2021.
International Search Report for Corresponding PCT Appln No. PCT/US2021/070751, mailed Sep. 10, 2021.

* cited by examiner

COOLING SYSTEM INTEGRATED WITHIN MODULAR, DETECTOR ELECTRONIC ASSEMBLY FOR A DIAGNOSTIC MEDICAL IMAGING APPARATUS

PRIORITY CLAIM

This application claims the benefit of priority of U.S. Provisional Application No. 63/198,079, filed Sep. 28, 2020, and entitled "A Quiet Cooling Design for a Long Axial FoV PET System", which is incorporated by reference in its entirety herein.

This application is a continuation in part of and claims the benefit of priority of an International Application filed in the United States Receiving Office, entitled "Cooling Channel With Non-Metallic Heat Sink For A Diagnostic Medical Imaging Apparatus", filed Aug. 26, 2020 and assigned serial number PCT/US2020/070462. This application is also a continuation in part of and claims the benefit of priority to a United States Application entitled "Method And Apparatus For Mounting And Aligning Detectors Of A Medical Imaging Apparatus", filed Jun. 25, 2020 and assigned Ser. No. 16/946,514. In National Phase jurisdictions permitting incorporation of patent documents by reference, such as the United States of America, the entire contents of both cited priority applications are hereby incorporated herein. Furthermore, all rights are reserved to amend this patent specification to incorporate the entire contents of both cited priority applications in jurisdictions that permit such amendment during National Phase prosecution before them.

TECHNICAL FIELD

This disclosure relates to cooling systems for medical imaging apparatuses. More particularly, this disclosure relates to modular, scalable fluid-cooling systems and methods for cooling gantries of medical imaging apparatuses, including gantries of long, axial field of view apparatuses.

BACKGROUND

Diagnostic medical imaging apparatuses include, by way of non-limiting example, computed tomography (CT), two-dimensional digital radiography (DR), magnetic resonance imaging (MRI), positron emission tomography (PET), single photon emission computed tomography (SPECT) modalities. Hybrid modality apparatuses include, by way of non-limiting example, PET/CT, PET/MRI, SPECT/CT, and SPECT/MRI, which combine in a single system the local imaging resolution benefits of CT or MRI and the sensitivity for imaging and detecting cellular and metabolic biological processes in a patient. Many of these imaging apparatuses or systems include a toroidal-shaped gantry structure through which is inserted a patient table. The gantry includes one or more circumferential rows and axially oriented columns of electromagnetic radiation detectors, which form a matrix-like detector array. The respective radiation detectors in the detector array emit electrons in response to incident photons of electromagnetic radiation. In some modalities, the incident photons are transmitted X-rays or ionized radiation emissions at the higher end of the electromagnetic frequency range (e.g., CT, DR, PET, SPECT), while in other modalities (e.g., MRI) the incident photons are within the radio frequency range. The output electrons of the detector elements in the detectors are processed by detector electronics to generate detector output signals, which are subsequently processed by the imaging apparatus to generate or construct patient images. In some imaging systems, detector electronics packages are housed with the detectors within the gantry structure in an integrated detector assembly.

Exemplary electromagnetic radiation detectors include photomultiplier tubes (PMTs) and solid-state detectors, such as avalanche photo diodes (APDs) and silicon photomultipliers (SiPMs). Signal gain of solid-state detectors are more temperature dependent than PMTs. The solid-state photon sensors and their detector electronics packages are typically maintained within relatively narrow temperature fluctuation and operational temperature bandwidths to reduce the likelihood of inaccurate detector readings and/or excessive noise generation components in the detector readings that otherwise might lead to poor quality patient images. The solid-state radiation detectors require external cooling to maintain detector assemblies within defined temperature fluctuation and bandwidth specifications. Typically, radiation detectors and detector assemblies in medical imaging systems are cooled by blowing cooling air over them, or by transferring detector heat to one or more conduits routed about the gantry structure that circulate cooling fluid in proximity to them.

In past cooling system designs for exemplary PET/CT scanning modalities, wherein the imaging apparatus gantry incorporates a PET axial field of view (aFOV) scanning zone that is axially aligned with a CT aFOV scanning zone, the cooling system was specifically sized to transfer heat from only one or two circumferential rows and axial columns of detector assemblies. Blown cooling air systems were satisfactory for such applications. However, recent movement in the field of PET imaging, with aFOV expansion of the patient imaging approaching one to two meters, has made it necessary to revisit the nature of both the design and the fabrication of such cooling systems, including in exemplary PET/CT systems. Often these axially expanded systems require cooling of a plurality of greater than two rows in each column of detector assemblies, further complicating blown cooling air-type cooling system architecture. Past cooling system designs for longer aFOV imaging systems have concatenated two or more existing, shorter aFOV cooling systems within the same gantry. In other words, conventional, known cooling system designs, modified for longer aFOV imaging systems, have utilized multiple water-to-air heat exchangers with fans to blow cooled air within the gantry, to transfer the heat out of the system back to the heat exchanger. This introduces two complexities to the design. The first one is limited space in the system. To remove the heat efficiently, the design might require adding larger and/or more heat exchangers in the gantry of the system. The second is related to noise generated due to the increased number of fans and the air flow required to remove the heat from the gantry of the extended aFOV imaging system. It becomes economically averse to fabricate medical imaging system gantry cooling systems for different combinations and orientations of detector assemblies (e.g., standard FOV systems with one or two/rows of such assemblies in each axially aligned column, versus extended, aFOV systems with more than two rows of detector assemblies per axial column).

SUMMARY

Exemplary cooling system embodiments described herein are modular and scalable to accommodate varying numbers of detector assembly orientations and geometries within gantry architectures of different medical imaging systems. Fluid cooled, modular components of the cooling systems are incorporated within individual detector electronic assemblies (DEAs). Exemplary coolant fluids include compressible and incompressible fluids such as liquids and gases (e.g., room air, nitrogen, water) or phase-change refrigerants. Each DEA includes therein a first chill plate for cooling detector elements and a second chill plate for cooling electronic components, such as printed circuit boards and/or power supplies. In some embodiments, each DEAs' first chill plate is thermally conductively coupled to cooling detector elements therein and the second chill plate is thermally conductively coupled to the other electronic components therein. Coolant flow cascades sequentially through the first chill plate and then through the second chill plate. In some embodiments, plural DEAs are interconnected in cascaded fashion, sharing a common, scalable coolant flow path. In various embodiments, any desired number of rows and columns of DEAs are selectively interconnected within the coolant flow path. In some embodiments, components of the fluid cooling system, such as liquid-liquid heat exchangers, pumps, and flow control valves, are located external the imaging system gantry. External location of such components conserves space within the gantry and reduces likelihood of coolant leak infiltration therein. Beneficially, in some system embodiments, including longer aFOV systems, flexible scaling of higher gantry heat loads is achieved, by increasing or decreasing the heat transfer capability of the external cooling system components in proportion to the number of DEAs within the gantry.

Aspects of this disclosure are directed to a fluid coolant system for a gantry of a medical imaging apparatus where the cooling system cools scalable detector electronic assemblies (DEAs) within the gantry. Each DEA includes within its modular housing a first chill plate thermally conductively coupled to cooling detector elements therein and a separate, second chill plate thermally conductively coupled to other electronic components, such as printed circuit boards and/or power supplies therein. In some embodiments, the first chill plate is oriented between the detector elements and the second chill plate, for thermally isolating the detector elements from other heat dissipating components within the DEA. In some embodiments, one or more of the first or second chill plates are segmented into plural sub segments, sharing a common coolant pipe. In some embodiments, coolant flow cascades sequentially through the first chill plate and then through the second chill plate. In this type of coolant flow path, the detector elements have cooling priority in the DEA over the other cooled components.

Exemplary embodiments disclosed herein feature a fluid coolant system for a medical imaging apparatus, having a gantry forming a patient tunnel; a cooling apparatus, coupled to and external the gantry, having a coolant supply for supplying fluid coolant to the gantry, and a coolant return for returning the coolant to the cooling apparatus. The imaging apparatus includes a detector electronic assembly (DEA) within the gantry, coupled to the cooling apparatus, having a housing; detector elements in the housing, for detecting incident photons of electromagnetic radiation originating outside of the housing and other electronic components in the housing. A fluid cooled, first chill plate is thermally conductively coupled to the detector elements, for cooling the detector elements. The first chill plate has a first inlet for receiving the coolant from the coolant supply and a first outlet for discharging the coolant to the coolant return. The DEA also includes a fluid cooled, second chill plate thermally conductively coupled to the other electronic components, for cooling the other electronic components. The second chill plate has a second inlet for receiving the coolant from the coolant supply and a second outlet for discharging the coolant to the coolant return.

Other exemplary embodiments disclosed herein feature a detector electronic assembly (DEA) for a medical imaging apparatus, including a housing; detector elements retained in the housing, for detecting incident photons of electromagnetic radiation originating outside of the housing; and other electronic components in the housing. The DEA includes a fluid cooled, first chill plate thermally conductively coupled to the detector elements, for cooling the detector elements, with the first chill plate having a first inlet for receiving fluid coolant and a first outlet for discharging the coolant. The DEA also includes a fluid cooled, second chill plate thermally conductively coupled to the other electronic components, for cooling the other electronic components, the second chill plate having a second inlet for receiving the coolant and a second outlet for discharging the coolant. The respective first and second inlets and outlets accessible outside the housing.

Additional exemplary embodiments of disclosed herein feature a method for scalable cooling of a gantry of a medical imaging apparatus, including: providing a gantry forming a patient tunnel; providing a cooling apparatus, coupled to and external the gantry, having a coolant supply for supplying fluid coolant to the gantry, and a coolant return for returning the coolant to the cooling apparatus The method includes providing a selected plurality of detector electronic assemblies (DEAs) for orientation within the gantry, with each respective DEA having a housing; detector elements in the housing, for detecting incident photons of electromagnetic radiation originating outside of the housing; and other electronic components in the housing, including a printed circuit board and a power supply. The provided DEA has a fluid cooled, first chill plate thermally conductively coupled to the detector elements, for cooling the detector elements, which is oriented in the housing intermediate the detector elements and the other electronic components. The first chill plate has a first inlet for receiving the coolant from the coolant supply and a first outlet for discharging the coolant to the coolant return. The provided DEA has a fluid cooled, second chill plate for cooling the other electronic components. The second chill plate has opposed first and second sides, respectively thermally conductively coupled to the printed circuit board on its first side and to the power supply on its second side. The second chill plate has a second inlet for receiving the coolant from the coolant supply and a second outlet for discharging the coolant to the coolant return. In some embodiments, one or more of the first or second chill plates are segmented into plural sub segments, sharing a common coolant pipe. In this method, the respective first and second inlets and outlets of the first and second chill plates are externally accessible outside of each respective DEA housing. The method includes orienting the plurality of DEAs within the gantry, so that their respective DEA housings are commonly coupled to a housing support of the gantry axially in sequence about an outside of the patient tunnel, parallel to a central axis defined by the patient tunnel; and that their respective detector elements face the patient tunnel, tangential to a circumference thereof, with components of the detector element projecting radially away from the patient tunnel. The method is further practiced by coupling the first inlet of the first chill plate of and the second inlet of the second chill plate of each DEA directly or indirectly to the coolant supply of the cooling apparatus; and coupling the first outlet of the first chill plate and the second outlet of the second chill plate of each DEA directly or indirectly to the coolant return of the cooling apparatus. Cooling capacity of the external cooling apparatus is scaled in proportion to the number of DEAs within the gantry that are cooled thereby. Coolant is circulated between the gantry and the cooling apparatus at a flow rate that maintains a specified stable temperature bandwidth for all detector elements in the each of the respective DEAs.

The respective features of the exemplary embodiments that are described herein may be applied jointly or severally in any combination or sub-combination.

BRIEF DESCRIPTION OF DRAWINGS

The exemplary embodiments are further described in the following detailed description in conjunction with the accompanying drawings, in which.

To facilitate understanding, identical reference numerals have been used, where possible, to designate identical elements that are common to the figures. The figures are not drawn to scale.

DESCRIPTION OF EMBODIMENTS

Figure 1:
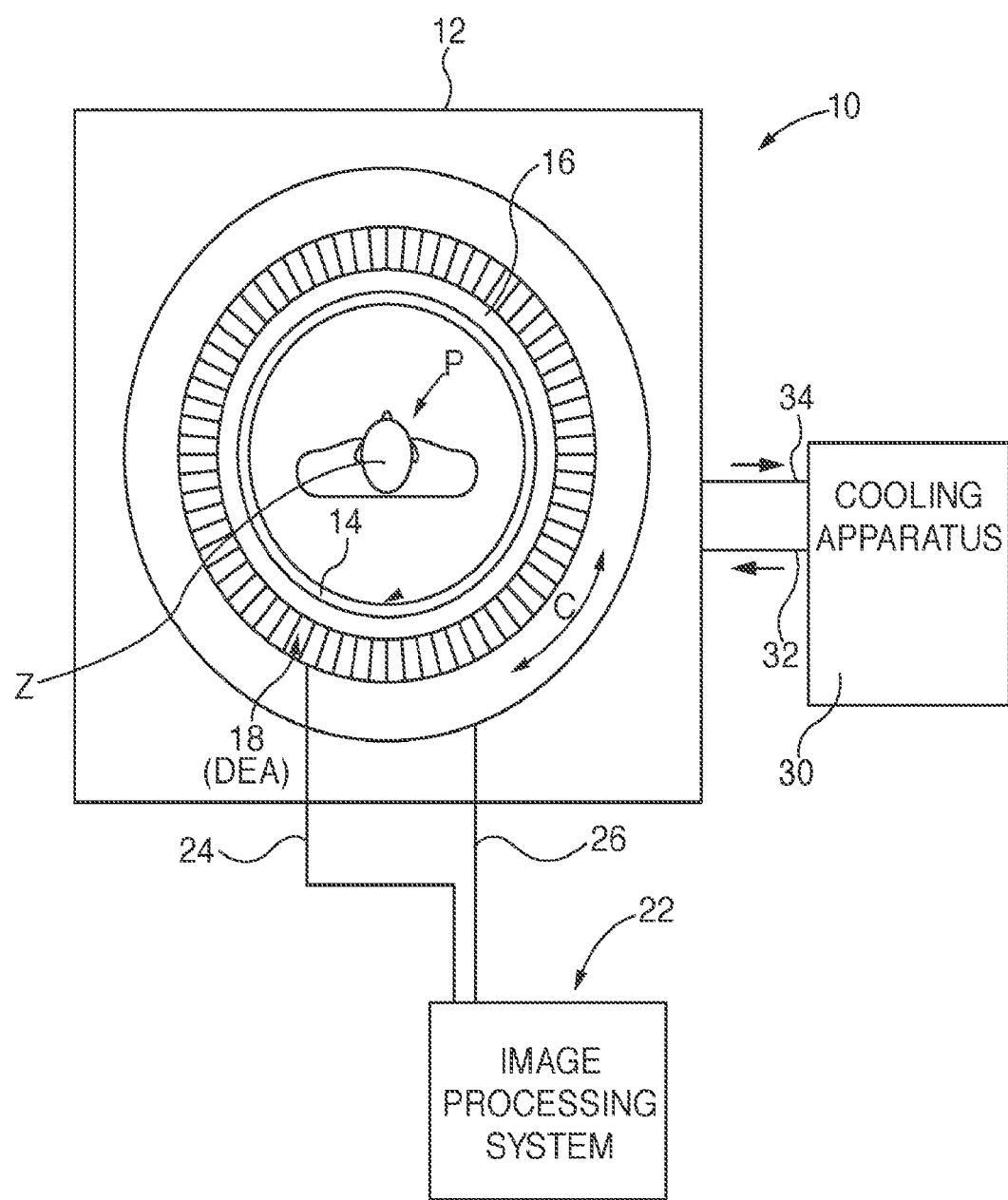
FIG. 1 is a front elevational view of a gantry of a combination PET/CT medical imaging scanner for generating PET and/or CT images of a patient, which incorporates a circumferential and axial matrix array of modular, detector electronics assemblies (DEAs), sharing a common cooling system.

Medical imaging apparatus with cooling systems incorporating cooling system embodiments described herein, in one or more of their modular, scalable detector electronics assemblies (DEAs), transfer heat out of system's gantry to maintain radiation detector and detector electronics within a designated temperature range, reducing the likelihood of temperature-related degradation of patient images. Various embodiments of these scalable, modular cooling systems are suitable for a broad range of axial field of view (aFOV) architecture applications, including computed tomography (CT), two-dimensional digital radiography (DR), positron emission tomography (PET), and single photon emission computed tomography (SPECT) modalities. Various embodiments of the cooling systems and their DEAs are also suitable for hybrid modality apparatuses that incorporate PET and another modality, (e.g., PET/CT or PET/MRI) of any length aFOV architecture.

Efficient cooling attributes of embodiments of these cooling systems are useful for DEAs that incorporate solid-state avalanche photo diodes (APDs) and silicon photomultipliers (SiPMs), as these types of solid-state detectors typically generate more operational heat than photo multiplier tubes (PMTs). Compared to PMTs, APDs and SiPMs are typically more susceptible to output signal distortion unless operated within relatively narrow temperature bandwidths. The scalable, modular cooling system embodiments described herein achieve high heat-load transfer out of the gantry of the imaging apparatus, facilitating operation of APDs and SiPMs within narrow temperature bandwidths, with less noise and construction complexity than known air-cooled systems.

The presently disclosed gantry cooling system embodiments transfer sufficient heat out of the gantry to maintain ambient operational temperature bandwidth and fluctuation specifications of the imaging system. More specifically, embodiments of the modular, scalable cooling systems disclosed herein efficiently transfer heat from the detector assembly of any modality of medical imaging apparatus by enhancing direct conductive heat transfer from radiation detectors, detector electronics and power supplies to gantry coolant in the cooling system. Cooling system components external the imaging system gantry dissipate heat from the gantry coolant. In this way, for specific aFOV length architectures, varying heat loads generated by varying numbers of DEAs are transferred out of the gantry by scaling the cooling system components located outside the gantry.

Some cooling system embodiments described herein facilitate fan-less direct water cooling of the electronics components, using thermal conductivity between the components and fluid-cooled, chill plate-type heat sinks as a heat transfer mode. Exemplary coolant fluids include compressible and incompressible fluids such as liquids and gases (e.g., room air, nitrogen, water) or phase-change refrigerants. The cooling system embodiments herein have overcome several design challenges. First, certain components such as the SiPM detector elements in the detector assemblies require lower and tighter temperature tolerances for the detectors to operate quantitatively within their design specifications. Second, electronics boards and other types of other electronic components associated with the detector assemblies, which also need to be cooled within the gantry, have irregular surface profiles and shapes that complicate capability of their direct contact with their associated, proximate, fluid-cooled heat sinks. Third, larger other electronic components in the DEA, such as power supplies are very bulky. Fourth, any fluid coolant leak within the gantry may cause electronics and power components therein to malfunction.

In various embodiments, modular, chill plate-type heat sinks are in direct contact with heat generating components. The chill plate has a fluid coolant line or conduit going through it with an inlet and an outlet. The plate material is selected for its thermal conductivity properties and may include one or more metals and/or thermally conductive ceramic compositions. Aluminum, and copper are typically used for the coolant lines. The coolant line takes several turns inside the plate to enhance heat transfer from plate to coolant. In some embodiments, the chill plate is designed as top and bottom plates with a groove for receiving the coolant line. Both plates are pressed against each other, sandwiching the coolant line therebetween, to enhance conductivity between the respective plate and its line. The term "chill plate", as used herein is intended to encompass solo, monolithic plates, as well as composite structures incorporating multiple subplates joined together to function as a unitary heat transfer medium, for absorbing heat generated or dissipated by an electronic component or other device within the associated DEA.

In some embodiments, the chill plates have a smooth external surface. In some embodiments, a thermal tape, or foam, or thermally conductive gel, or the like is interposed as a heat transfer median between the chill plate and its associated heat-generating detector elements, electronics board, or power supply. In other embodiments, the outer surface of the chill plate is fabricated to have the opposite, mirror image surface topography of its associated circuit board pattern, where the valleys in the chill plate profile encapsulate integrated circuit (IC) or other components on the circuit board that have high heat dissipation. In such embodiments, a thermally conductive material, such as thermal tape or foam, thermal grease or gel, or the like, is interposed as a thermal median between the plate surface and the associated component to aid the transfer of the heat from the component to the chill plate.

Embodiments of the cooling systems have scalable architecture, with one or more modular detector electronics assemblies (DEAs), allowing for axial FoV scalability of various imaging system configurations. Furthermore, having a DEA as a self-sufficient design in a housing with integrated input/output (I/O) communication of control/data information capability, electric power supply, chill plates with fluid coolant inlets and outlets, consolidates detector elements of detectors, electronics, and power supplies into one cohesive package. These DEA embodiments package the main heat generators/dissipators in the gantry of the imaging system, such as the detector electronics, other electronic component boards or printed circuit boards and power supplies into one package with its own dedicated cooling system components. In some embodiments a DEA's power supply is thermally coupled to a chill plate, to remove the heat from the former. By packaging other electronic components, such as the power supply, electronic boards, and printed circuit boards in the same housing as the detector elements, the integrated DEA is more compact, can share one or more chill plates among heat generating components, and minimize the number of coolant line connections between chill plates. In some DEA cooling system embodiments, a first chill plate is thermally coupled to a detector array of detector elements, and a second chill plate is thermally coupled to other electronic components, such as electronics board and a power supply. In some embodiments, the first chill plate is oriented within the DEA housing between the detector array of detector elements and the second chill plate, with the latter's associated other electronic components, such as electronics boards and power supplies.

In some embodiments the scalable cooling system is a closed loop system. This design has great advantages such as having a finite amount of coolant, such as water, that does not flood the system and facility if and where there is a leak, as compared to an open loop system with a relatively infinite coolant flow capability. This also allows the cooling system to provide stable coolant temperature to the chill plates within the DEAs, as ADP or SiPM components in their detector arrays require relatively narrow temperature bandwidth to operate quantitatively. In some imaging system embodiments, the specified coolant temperature bandwidth is 23° C. with +/−2° C. to maintain a stable temperature to the SiPMs within the DEAs.

In some embodiments, coolant flowing to the gantry from the cooling apparatus is initially provided to the first chill plate associated with the detectors elements to maintain a tighter, stable temperature bandwidth on the SiPMs in the array. The output of the first chill plate is then plumbed to the second chill plate in the DEA, associated with the electronics and power supply. In some cooling system embodiments, where multiple DEAs are cascaded in the axial direction, the same flow sequence of coolant first flowing to the first chill plate in each DEA, then sequentially each second chill plate is maintained, for all DEAs in the cascade chain. Namely, coolant from the cooling apparatus first flows to the inlet for the first DEA in the cascade, then to the inlet of the second DEA in the cascade, and so on. In the last DEA in the cascade, its outflow from the outlet of its first chill plate is plumbed to its second chill plate. The cascade continues backwards, or upstream back to the return line of the cooling apparatus by routing coolant to and out of each successive second chill plate in the cascade, back to the first DEA in the chain. Thereafter, coolant discharged from the outlet of second chill plate of the first DEA is routed back to the cooling apparatus.

In some embodiments, to ensure all the DEAs in each axially interconnected column in the cooling system about the circumference of the gantry receive the same input coolant temperature, the coolant is branched out from the coolant supply to each DEA column via an annular ring manifold. In another alternative embodiment, coolant is branched out from the coolant supply to each interconnected DEA within an annular row or ring about the gantry circumference.

With reference to the figures, FIG. 1, shows a PET/CT imaging apparatus or system 10 for generating an overlaid PET and CT image display of a patient P. The apparatus 10 includes a gantry 12. A patient tunnel wall 14 in the gantry 12 defines an axial direction axis Z, extending orthogonally in relation to the plane of the drawing of FIG. 1. The patient tunnel wall 14 is circumscribed by an acoustic foam liner 16. A plurality of modular, detector electronics assemblies (DEAs) 18 are arranged coaxially in a matrix-like axial (Z direction) and circumferential (C directional arrow) array outside the patient tunnel wall 14 and the acoustic foam liner 16, equally radially spaced from the axis Z. An image processing system 22 is coupled to each DEA 18 by a communication and control signals pathway 24 and a power conduit 26. A cooling apparatus 30, oriented external the gantry 12 circulates fluid coolant through one or more of the DEAs 18, in a closed cooling loop, via coolant supply conduit 32 and fluid return conduit 34. Exemplary coolant fluids include compressible and incompressible fluids such as liquids and gases (e.g., room air, nitrogen, water) or phase-change refrigerants.

Figure 2:
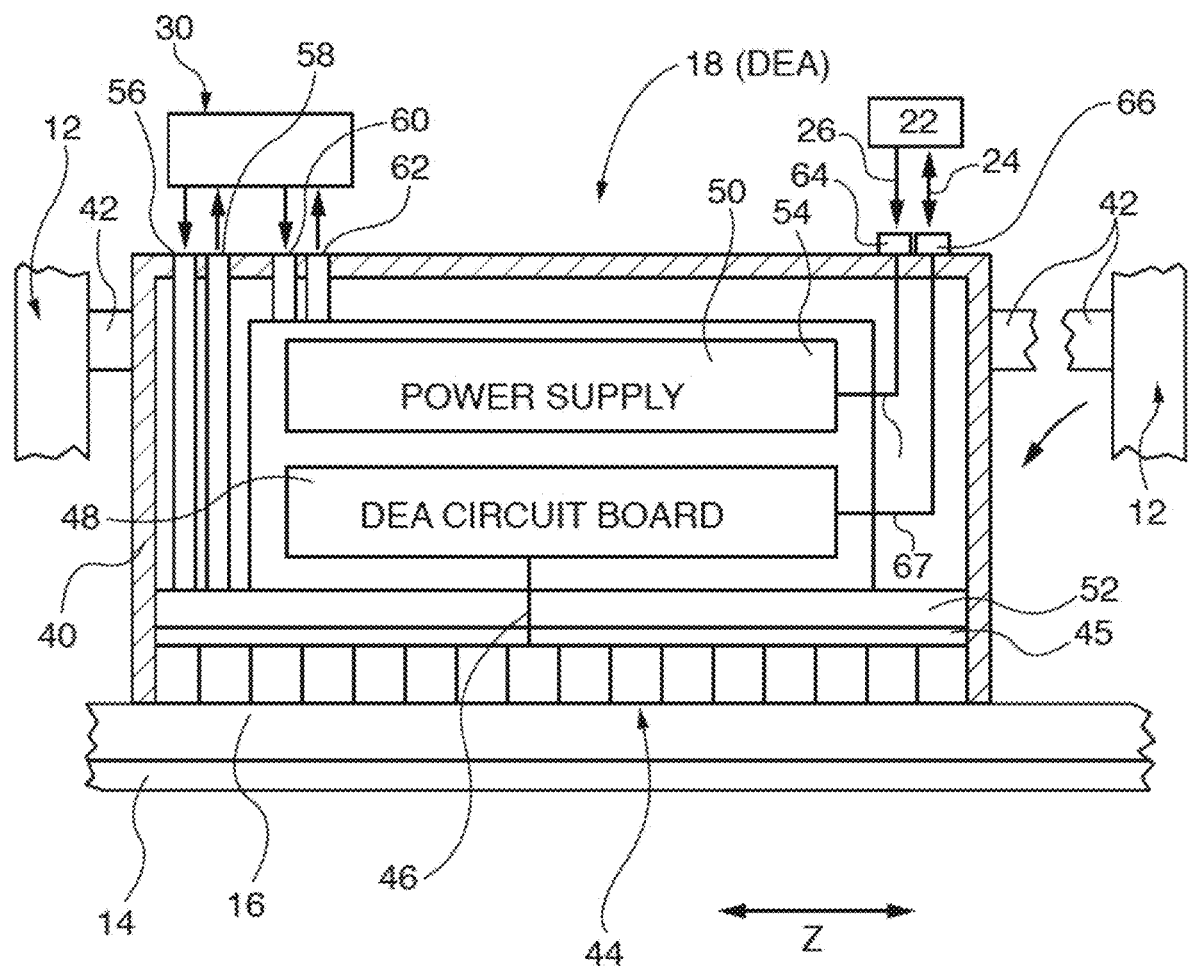
FIG. 2 is a schematic, side elevational cross section of a single, modular, DEA of the PET/CT scanner of FIG. 1.
Figure 3:
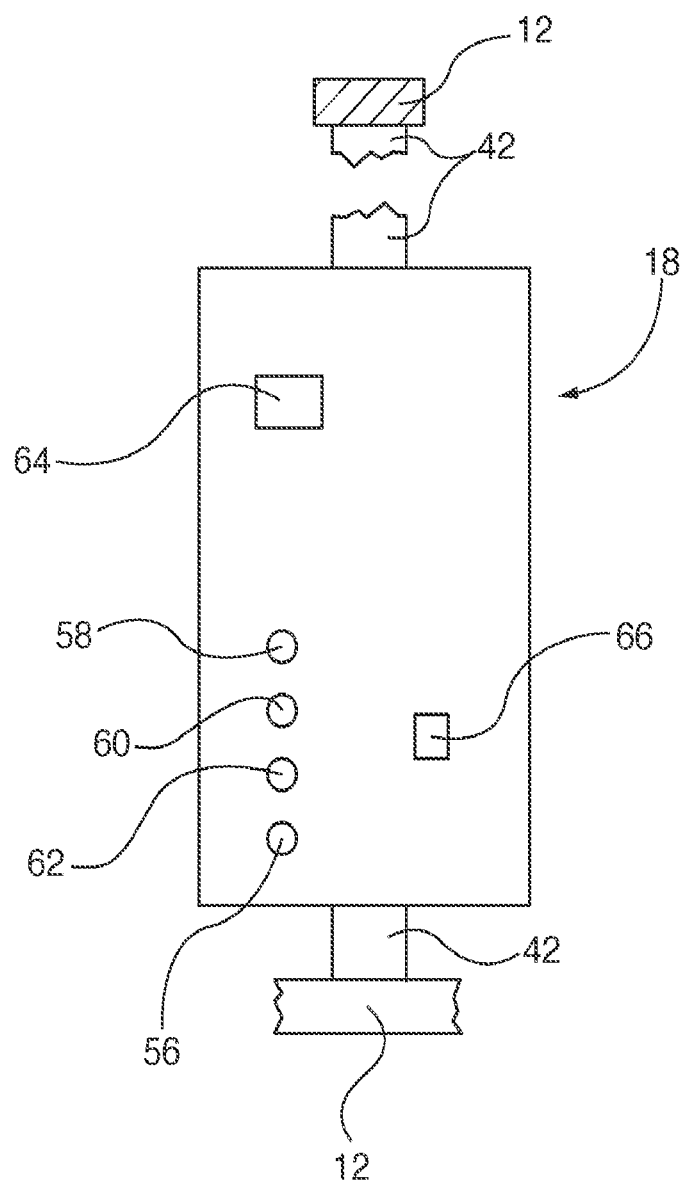
FIG. 3 is a top plan view of the DEA of FIG. 2.

Referring to FIGS. 2 and 3, exemplary DEAs 18 comprise a modular DEA housing 40, coupled to the gantry 12 by a housing support 42. An exemplary DEA modular housing and housing support comprises a detector head, pivotable detector bearing and mounting rail as shown and described in co-pending U.S. application Ser. No. 16/946,514. In jurisdictions permitting incorporation of patent documents by reference, the entire contents of application Ser. No. 16/946,514 is hereby incorporated herein. The DEA housing 40 includes a plurality of radiation detector elements 44, clustered in a two-dimensional array facing the patient P. Exemplary radiation detector elements 44 include avalanche photo diodes (APDs) or silicon photomultipliers (SiPMs). A detector data acquisition (DDA) package 45, for example incorporated on a printed circuit board, receives signals from the individual radiation detector elements 44 that are indicative of photons sensed by their detector crystals. The received detector crystal signals are routed from the DDA package 45, via a detector data-signal pathway 46 (e.g., a plug-in terminal-type, electrical connector), to a DEA electronic circuit board 48 for further signal processing. Some electronic circuit boards in the DEA incorporate printed circuit boards.

The DEA electronic circuit board 48 generates respective detector output signals, which are routed to the image processing unit 22, via a communications port 66 on the DEA housing 40 that interconnects an internal logic signals pathway 67 to the communication and control signals path 24. The detector output signals are subsequently processed by the image processing unit 22 to generate or construct patient images. In some embodiments, DDA package functionality is incorporated within the DEA circuit board rather than as a separate component. The DEA 18 also incorporates an internal DEA power supply 50. A power inlet 64 on the DEA housing 40 interconnects a power cable 65 of the power supply 50 to the external power conduit 26. Each DEA 18 is a self-contained modular unit, incorporating radiation detector elements 44, the electronics DDA 45, and related other electronics, (including by way of example the DEA electronics board or circuit board 48 to acquire and process signals indicative of incident photons sensed by the detectors, and routing output signals to the image processing unit 22, and the internal DEA power supply 50). Accordingly, any desired number of the individual, modular DEAs 18 are readily combined, by coupling each of its respective power inlet 64 and communications port 66 on the housing 40 into its respective complementary power conduit 26 and communication and control signals path 24 within the gantry 12, to create scalable two-dimensional matrices of detector elements 44 for any diameter and axial length patient tunnel wall dimensions within the gantry; including those of extended aFOV imaging apparatuses.

The modular DEA 18 also incorporates scalable cooling system architecture, complementary to the previously described scalable detector element 44 architecture. Varying heat transfer loads for different arrays of modular DEAs 18 are accommodated by altering the heat transfer capacity of the external cooling apparatus 30, rather than by altering internal structure of each DEA. The internal cooling system components in the DEA housing 40 comprise a fluid-cooled, first chill plate 52, oriented proximate the heat-generating radiation detector elements 44 and/or the DDA package 45, and a second chill plate, oriented proximate the heat-generating "other electronic components" (e.g., the DEA circuit board 48 and power supply 50).

Figure 4:
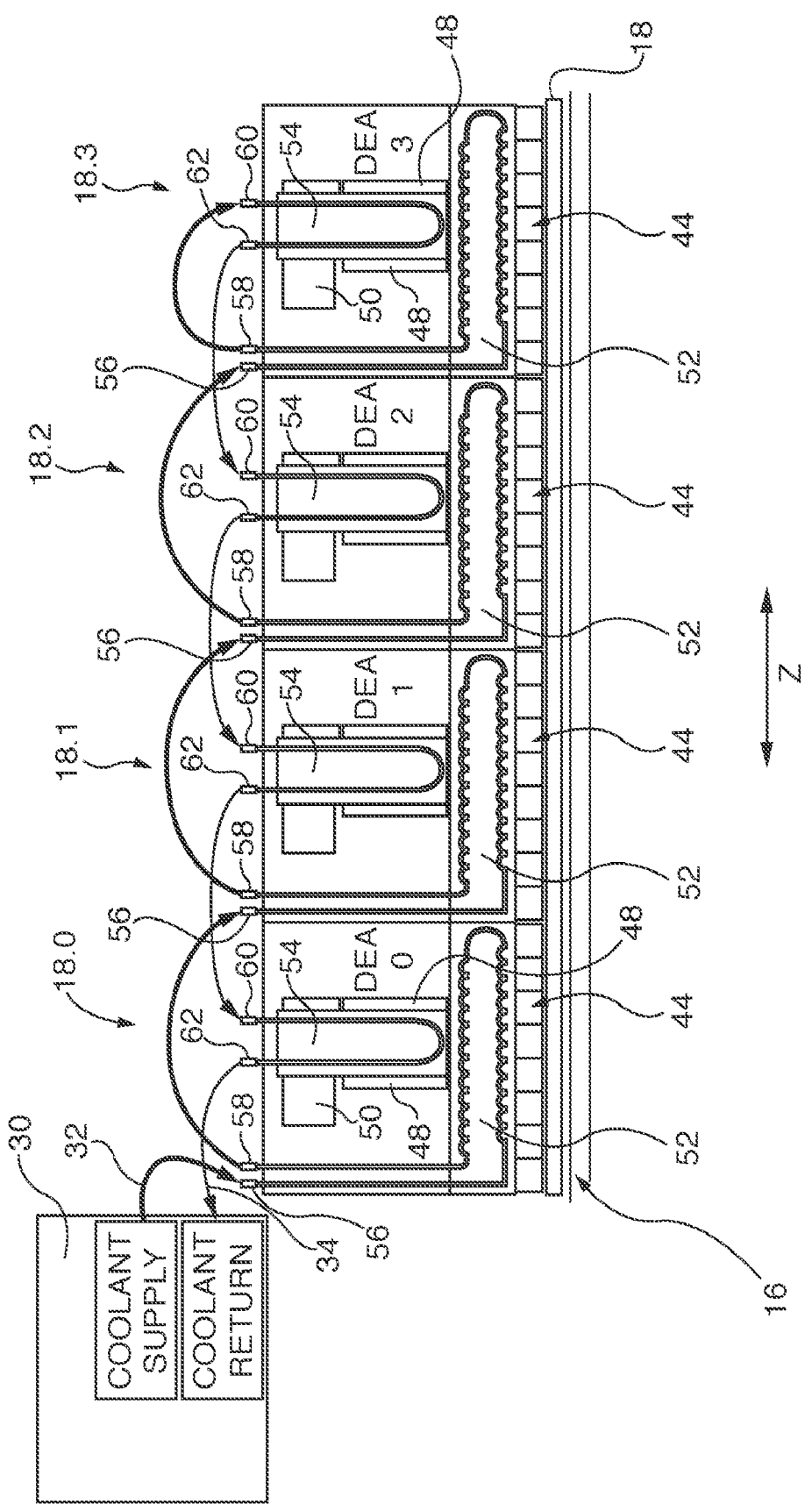
FIG. 4 is a schematic, elevational cross section of an axial row of four of the DEAs of FIG. 2 in the PET/CT scammer of FIG. 1, showing a cascading coolant flow loop of the cooling system.

In the embodiment of FIGS. 2-4, the first chill plate 52 is oriented generally parallel to the detector elements 44 and interposed between them and the relatively higher heat-generating "other electronic components" DEA circuit board 48 and power supply 50. This first chill plate 52 orientation provides additional heat shielding for the relatively more temperature sensitive detector elements 44. The second chill plate 54 is oriented generally perpendicular to and radially inwardly from the first chill plate 52, spanning almost the entire width and height of the DEA housing 40. This orientation of the second chill plate 54 provides a relatively large surface area and thermal mass for enhancing heat transfer from any other electronic components in the DEA, including by way of example the circuit board 48 and power supply 50. While the first 52 and second 54 chill plates shown in FIGS. 2-4 are generally planar, in other embodiments one or more of the chill plates, or sub-plate components thereof that are joined into a unitary, composite chill plate have non-planar profiles. Non-planar profile chill plate embodiments are suitable for wrapping around multiple surfaces of a heat generating/dissipating electronic component or other component.

To enhance direct, conductive heat transfer within the DEA 18, in some embodiments one or both of the first 52 and second 54 chill plates are at least partially in direct abutting, thermally conductive contact with their proximate heat-generating components. In other embodiments, one or both of the first 52 and second 54 chill plates are oriented in opposed, mutually spaced relationship with their proximate heat-generating components. To enhance conductive heat transfer across mutually spaced, opposed components, selectively, all or portions of the gaps therebetween are filled with a thermally conductive material median, such as thermally conductive sheet foam, tape, gel or grease.

Referring to FIGS. 1-3, the first 52 and second 54 chill plates transfer heat absorbed from their respective, proximate radiation detectors 44, DDA package 45, other electronic components, including the DEA circuit board 48, or power supply 50 to fluid coolant that is circulating within a closed loop between the gantry 12 and the external cooling apparatus 30. Within each DEA 18, the first chill plate 52 receives circulating fluid coolant entering through a first coolant inlet 56. Coolant flows through an internal conduit formed within the first chill plate 52, absorbing heat from the plate material by conductive and convective heat transfer modes and is discharged out of a first cooling outlet 58. Similarly, within each DEA 18, the second chill plate 54 receives circulating fluid coolant entering through a second coolant inlet 60. Coolant flows through an internal conduit formed within the second chill plate 54, absorbing heat from the plate material by conductive and convective heat transfer modes and is discharged out of a second cooling outlet 62.

In some cooling system embodiments, respective inlets 56, 60 and outlets 58, 62 of the first 52 and second 54 chill plates communicate directly and independently with the cooling loop in the gantry 12, with parallel respective coolant flow paths for each DEA 18. In some medical imaging applications, it is desirable to minimize the number of coolant conduits in the gantry 12, to reduce likelihood of coolant leak damage to equipment. In some cooling system embodiments, providing cascading, serial coolant flow from the coolant supply conduit 32 of the cooling system 30, through the first chill plate 52, then the second chill plate 54 and back to the coolant return conduit 34 simplifies the cooling path and reduces the quantity of conduits, compared to cooling systems relying on independent, parallel coolant flow to each DEA. In other embodiments, the scalable, modular DEA 18 is used in a single component application (e.g., as a detector for a digital radiography imaging device). Referring to the DEA 18 shown in FIGS. 2 and 3, and the fluid flow path of DEA 18.3 of FIG. 4, in such single-component DEA applications, coolant from the coolant supply 32 of the cooling apparatus 30 enters the first coolant inlet 56 of the first chill plate 52, exits its first coolant outlet 58, enters the second coolant inlet 60 of the second chill plate 54 and exits its second coolant outlet 62, for discharge into the coolant return 34 of the cooling apparatus.

In the cooling system embodiment of FIG. 4, four DEAs, designated 18.0, 18.1, 18.2 and 18.3 are sequentially cooled in a cascading flow path, wherein DEA 18.0 is the first, most upstream DEA relative to the cooling apparatus 30 and DEA 18.3 is the last, most downstream DEA in the flow path. Components in each of the DEAs and coolant flow paths are shown schematically. All four of the respective first chill plates 52 receive coolant sequentially in a cascading fashion, in the direction of the flow arrows shown in the figure. The first DEA 18.0 in the cascading flow sequence receives flowing coolant from the coolant supply conduit 32 via the first inlet 56 of its first chill plate 52, which then exhausts the coolant via the first outlet 58. The coolant exhausted from the first outlet 58 of the first chill plate 52 of DEA 18.0 then enters DEA 18.1 via the first inlet 56 of its first chill plate 52, exhausting out of the latter's respective first outlet 58. Sequentially, coolant exhausting DEA 18.1 enters into and exhausts out of DEA 18.2, via the latter's first inlet 56 and first outlet 58 of its respective first chill plate 52. After exiting DEA 18.2, the coolant enters into the last, furthest downstream DEA 18.3 in the cascading fluid flow path, via the latter's first inlet 56 its respective first chill plate 52. By now, the first chill plate 52 in each and all of the respective DEAs 18.0-18.3 have been cooled.

Coolant returns to the cooling apparatus 30 by cascading flow through the second chill plates 54 of each of the respective DEAs in reverse order, from DEA 18.3 back to DEA 18.0 and the coolant return conduit 34, completing the coolant loop. Focusing now on the last downstream DEA 18.3 in the coolant flow path, coolant exhausted from the first outlet 58 of its first chill plate 52 flows into the second coolant inlet 60 of its second chill plate 54 and exhausts from the second coolant outlet 62. Thereafter, the coolant exiting DEA 18.3 flows back upstream toward the coolant return conduit 34 of the cooling apparatus 30, in cascading fashion, by entering the second coolant inlet 60 and exiting the second coolant outlet 62 of the second chill plate 54 of upstream DEA 18.2. Thereafter, in sequence, the coolant enters the second coolant inlet 60 and exits the second coolant outlet 62 of the second chill plate 54 of the next upstream DEA 18.1. Finally, the coolant enters the second coolant inlet 60 and exits the second coolant outlet 62 of the second chill plate 54 of the first upstream DEA 18.0, whereupon the now heated coolant returns and recirculates back to the cooling apparatus 30, via the coolant return conduit 34.

Figure 5:
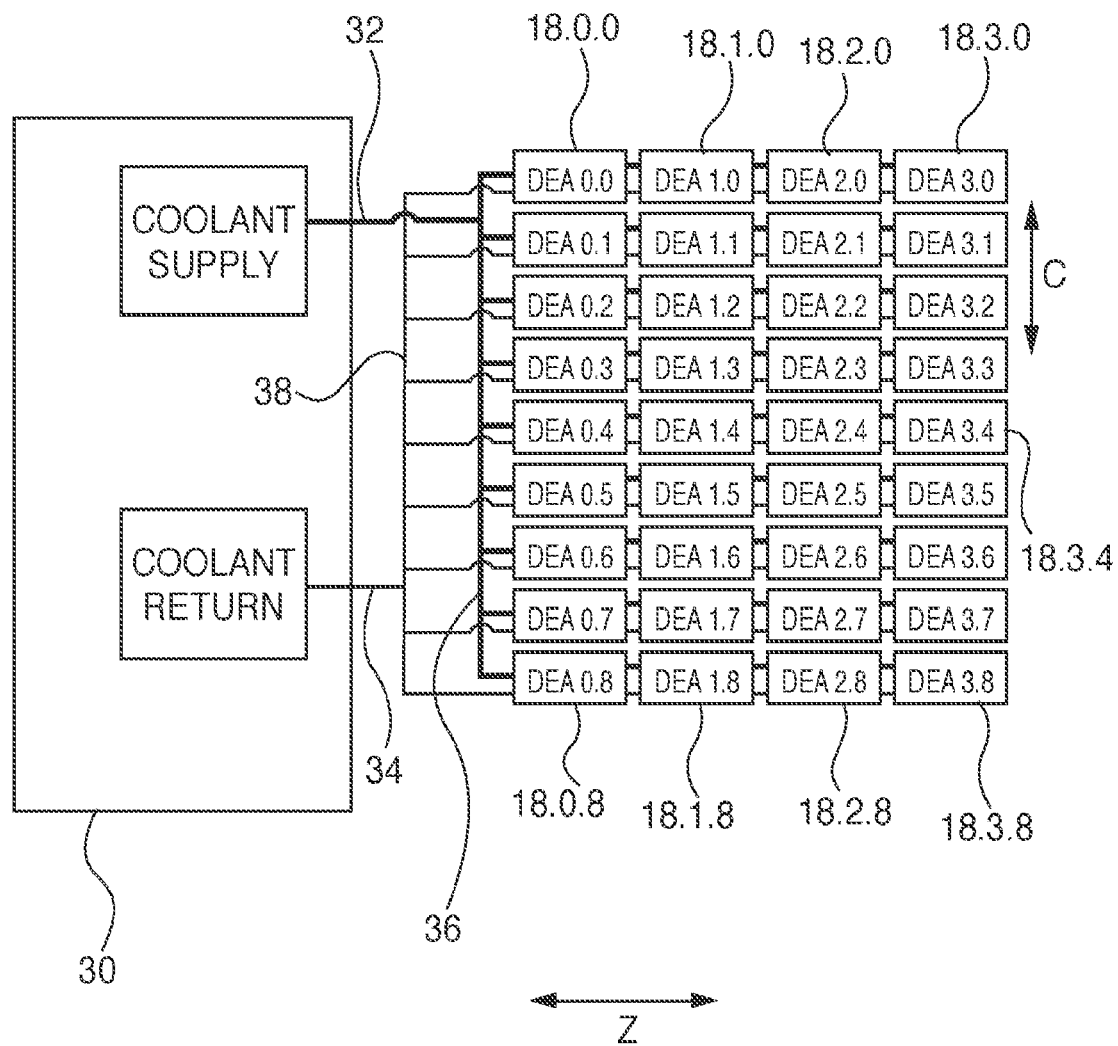
FIG. 5 is a schematic, flat projection of a two-dimensional matrix grid of the circumferential array of the modular, DEAs of the medical imaging apparatus of FIG. 1, showing their cascading coolant flow loop of the cooling system among axial columns of the assemblies.

The described cascading, cooling flow path of FIG. 4 is scalable to accommodate any desired number of rows or columns of DEAs in the gantry 12. While four cascading DEAs 18.0, 18.1, 18.2 and 18.3, are shown in FIG. 4, other embodiments of cooling systems that incorporate the described cascading cooling flow path have fewer or greater numbers of DEAs. In some cooling system embodiments, the cascading cooling flow sequence of DEAs and their associated cooling system coolant conduits are selectively aligned in one or more columns, axially along the Z axis of the gantry 12, as shown in FIG. 5. The designated position of each DEA 18 in the matrix of detectors is DEA $\Delta.\Theta$, where $\Delta$ is the circumferential row in the directional axis C and $\Theta$ is the axial column in the directional axis Z. The bold line, coolant supply conduit 32 branches off, via an annular supply manifold 36 in parallel to each of the columns, designated DEA $\Delta.0$ to $\Delta.8$, feeding coolant, in cascading fashion, to each respective downstream, first chill plate in the associated column. Coolant exiting the first outlet of each respective, first chill plate of the last downstream DEA 3.0 to 3.8 in turn is routed to the second inlet of its corresponding respective second chill plate, and sequentially back upstream, from its respective second outlet to the outlet of the next upstream corresponding DEA 2.0 to 2.8, thereafter upstream to corresponding DEA 1.0 to 1.8, and lastly to the first upstream corresponding DEA 0.0 to 0.8. Coolant exiting the corresponding second outlet of the second chill plate in DEAs 0.0 to 0.8 flows in parallel, via annular return manifold 38 back to the coolant return 34 of the coolant system 30. In other cooling system embodiments, the cascading coolant flow path from the coolant supply 32 to the coolant return 34 of the cooling system 30 is parallel among the circumferential rows or rings of DEAs $0.\Theta$ to $3.\Theta$ (not shown in the figures).

Figure 6:
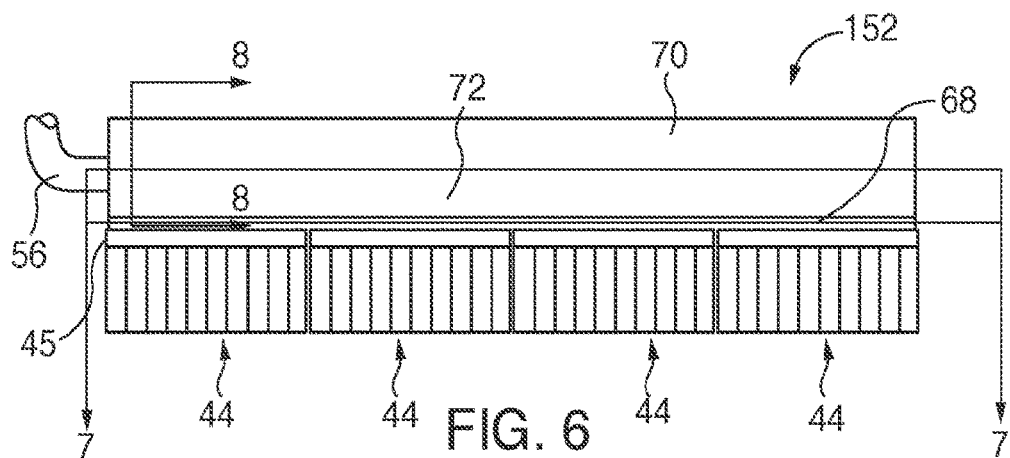
FIG. 6 is a schematic elevational view of detector arrays and a first detector chill plate of the DEA of FIG. 2.
Figure 7:
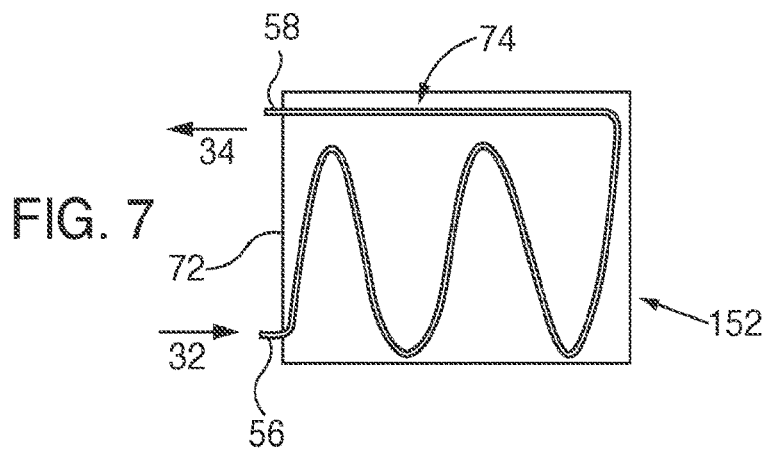
FIG. 7 is a plan cross-sectional view of the first detector chill plate of FIG. 6.
Figure 8:
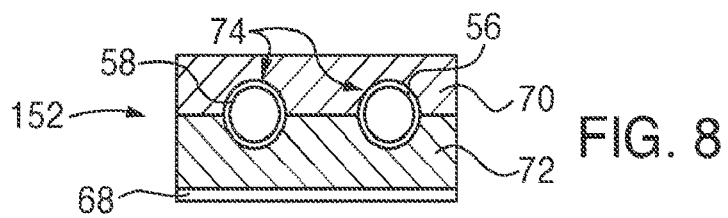
FIG. 8 is an elevational cross-sectional view of the first detector chill plate of FIG. 6.

FIGS. 6-8 show another exemplary embodiment of a first chill plate 152, wherein a thermally conductive foam layer 68 fills gaps or voids between that chill plate and its corresponding, opposing detector element components of the detector elements 44 and DDA 45. In other embodiments, other thermally conductive material, such as thermally conductive tape, thermal gel and/or thermal grease substitutes for or is used in conjunction with the thermal foam layer 68. The first chill plate 152 is a split-construction, joined composite of a top plate 70 and a bottom plate 72. A coolant pipe 74 forms the first coolant inlet 56 and the first coolant outlet 58; it is in thermally conductive communication with and sandwiched between the thermally conductive top 70 and bottom 72 plates. Inwardly facing, opposing surfaces of the top 70 and bottom 72 plates conform to the outer surface profile of the corresponding coolant pipe 74, for direct contact therebetween, or with any gaps or voids filled with thermally conductive material. In various embodiments, the conforming profiles of inwardly facing, opposing surfaces of the top 70 and bottom 72 plates are formed by known casting, molding, 3-D printing and/or machining manufacturing process. In some embodiments, the first chill plate 52 is cast or molded in place about the coolant pipe 74, without the need for a sandwiched construction with joined separate top 70 and bottom 72 plates. In plan form, such as the serpentine-axial profile shown in FIG. 7, the coolant pipe 74 is formed in any desired axial profile that enhances conductive heat transfer from the top 70 and bottom 72 plates to coolant flowing through the pipe. The chill plate 52, including its top 70 and bottom 72 plates and its coolant pipe 74 are constructed of thermally conductive material. In some embodiments, the chill plate is constructed as shown and described as a cooling channel and heat sink in co-pending International Application No. PCT/US2020/070462. In jurisdictions permitting incorporation of patent documents by reference, the entire contents of International Application No. PCT/US2020/070462 is hereby incorporated herein.

Figure 9:
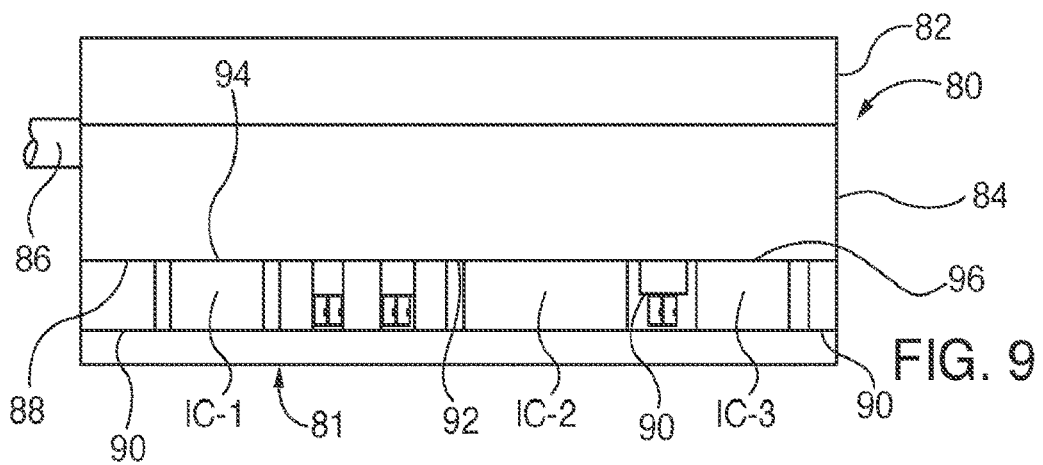
FIG. 9 is a side elevational view of an alternative embodiment of a chill plate.

FIG. 9 is another embodiment of a chill plate 80 for absorbing heat generated by a proximate circuit board 81. The chill plate 80 has a sandwiched construction like that of the first chill plate 152 of FIGS. 6-8. The opposing joined second top plate 82 and second bottom plate 84 capture a second coolant pipe 86 therebetween. To enhance conductive heat transfer from the opposing circuit board 81, one or more regions of the bottom face 88 of the second bottom plate 84 have formed elevational surface profiles that are mirror images of the elevational surface profile of a corresponding region of the circuit board. In some regions, the bottom face 88 forms a post or island 90 projecting outwardly therefrom, towards the circuit board 81. In other regions the bottom face 88 forms a well or cavity 92 that receives a component, such as the integrated circuit packages IC-2 and IC-3 projecting from the circuit board 81. At the region 94 of the bottom face 88, the integrated circuit package IC-1 is in direct abutting contact with the chill plate 80. At the region 96, the integrated circuit package IC-3 is spaced away from the opposing bottom face 88; the gap therebetween is filled with thermally conductive grease or gel, or any other desired thermally conductive filler material.

Figure 10:
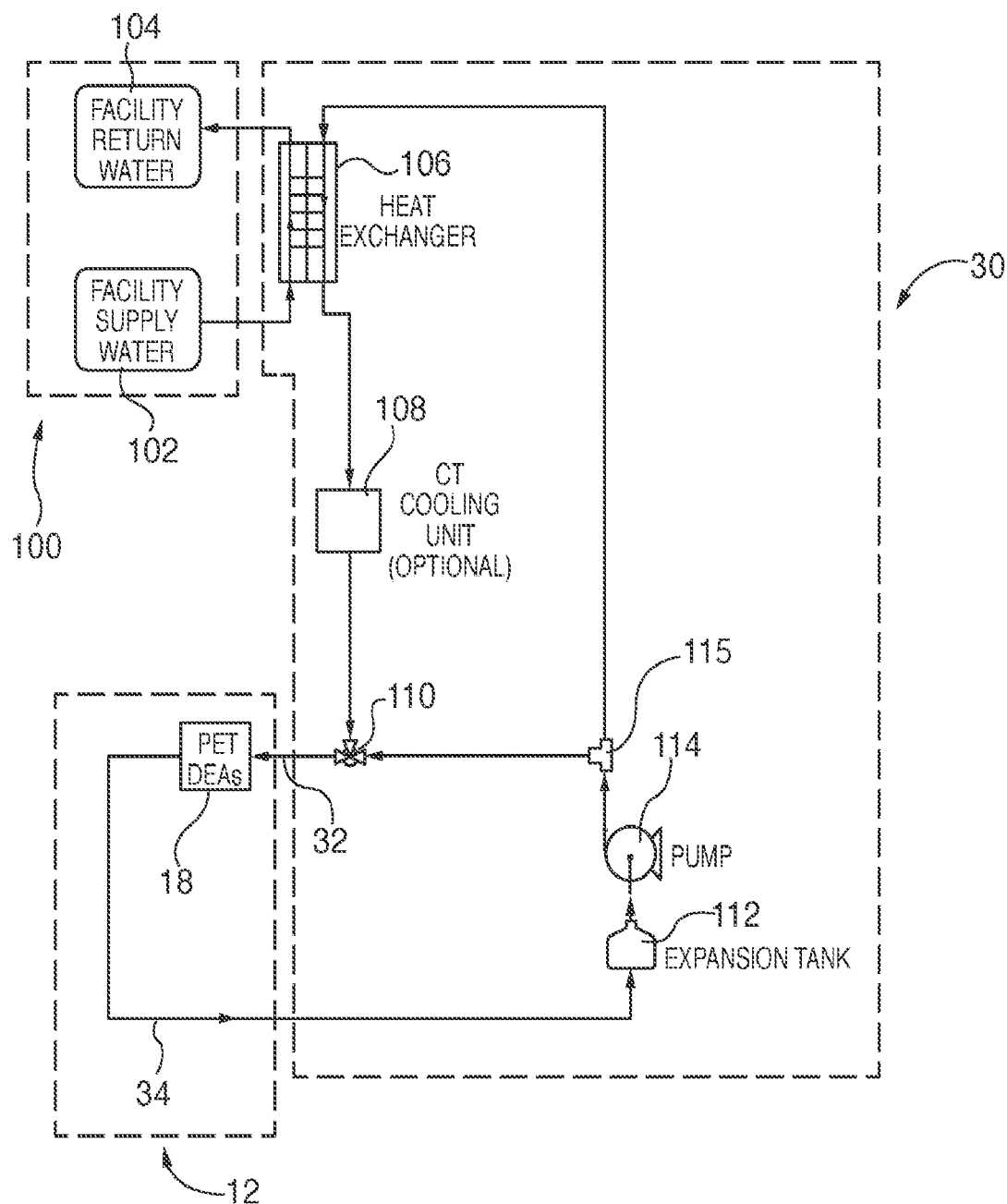
FIG. 10 is a schematic of the cooling system of the PET/CT scanner of FIG. 1.

FIG. 10 is a schematic of an exemplary embodiment of a cooling apparatus 30 of the extended aFOV, PET/CT modality, medical imaging apparatus 10, comprising a fluid, continuous flow, closed coolant loop, circulating a liquid coolant such as water or a compressed, gaseous coolant, such as nitrogen or compressed air. In other embodiments, the coolant is a mixed phase, liquid/gas refrigerant, in which case the cooling apparatus incorporates a refrigeration system with an expansion valve, compressor, condenser and the like (not shown). In general, flowing coolant in the coolant loop absorbs heat generated by various components within the gantry 12, such as the exemplary DEA 18, and transfers the absorbed heat to a heat sink.

Here, the heat sink is a facility water system 100, which provides a flowing, cool water supply 102 into an intake loop of a liquid-liquid heat exchanger 106; thereafter, warmer return water 104 exits the heat exchanger. The previously circulated, heated coolant from the gantry 12 flows through a corresponding outlet loop of the heat exchanger 106, transferring heat to return water 104. In some embodiments, coolant exiting the heat exchanger 106 passes through an optional CT cooling unit 108 before entering a tee-type mixing valve 110.

The mixing valve 110 selectively mixes proportionally cooled coolant that has passed through the heat exchanger 106 and relatively hotter coolant from the coolant return conduit 34 to achieve a desired coolant temperature. Coolant of the desired coolant temperature exits the mixing valve 110 into the coolant supply conduit 32, where it enters the gantry 12, absorbs heat from the DEAs 18 and any other, if any, cooled components in the gantry. More specifically, the coolant in the coolant supply conduit 32 passes through the previously described first and second chill plates of one or more of the DEAs 18, where it absorbs heat generated by various internal detector elements, circuit electronic boards and power supplies, etc. The now heated coolant returns to the cooling apparatus 30 via the coolant return conduit 34. The heated coolant received from the coolant return conduit 34 is stored in an expansion tank 112. Circulating pump 114 pumps the still heated coolant through the coolant loop through bypass tee 116, where a portion of the heated coolant flows to the heat exchanger 106, for subsequent refresh cooling and the remaining portion of the heated coolant is routed to the mixing valve 110. The mixing valve 110 and the pump 114 adjust flow rate and mixing proportions of the recirculating coolant to achieve desired heat absorption from the gantry. One specific coolant temperature control parameter of interest is maintaining a stable temperature bandwidth of the detector elements in each DEA within specification parameters, to avoid detector distortion. In some imaging system embodiments, where its DEAs incorporate SiPM detector elements, the coolant temperature bandwidth is 23° C. within +/-2° C. The mixing valve 110 and the pump 114 circulate the coolant between the gantry 12 and the cooling apparatus 30 at a flow rate that maintains a specified stable temperature bandwidth for all detector elements in the each of the respective DEAs 18 in the gantry.

Heat absorption and transfer capacity of the external cooling apparatus 30 is proportionately scaled to the number of modular DEAs 18 in the gantry 12. As each modular DEA 18 incorporates its own dedicated internal cooling components (e.g., its first and second chill plates and their related coolant inlets and outlets), there is no need to add additional configurations of auxiliary cooling devices, such as cooling fans, to the gantry 12, when changing the number of DEAs in the gantry for different imaging scanning field dimensions.

Figure 11:
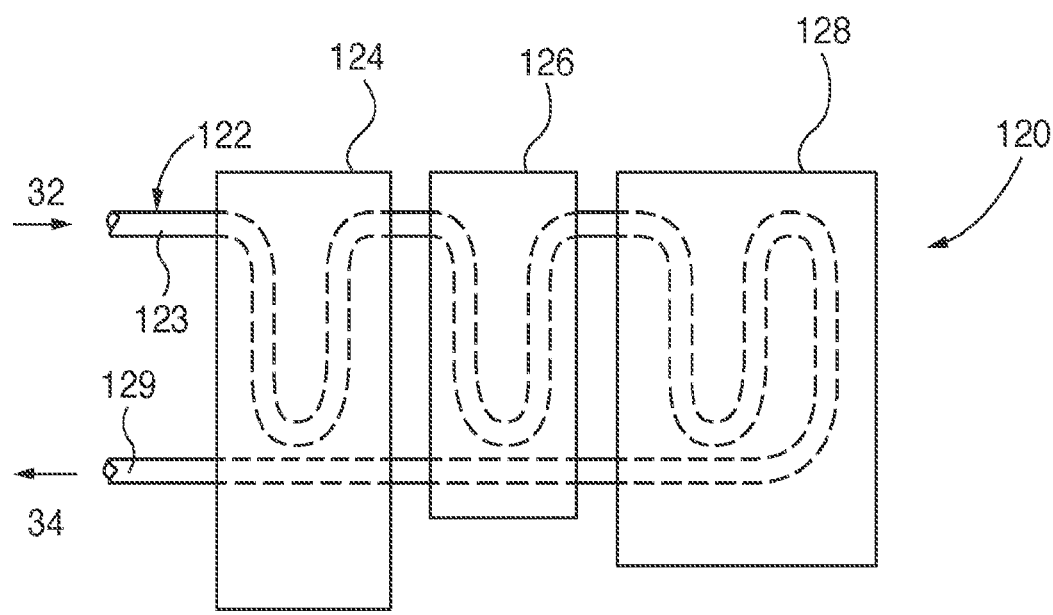
FIG. 11 is a plan view of a segmented first or second chill plate.
Figure 12:
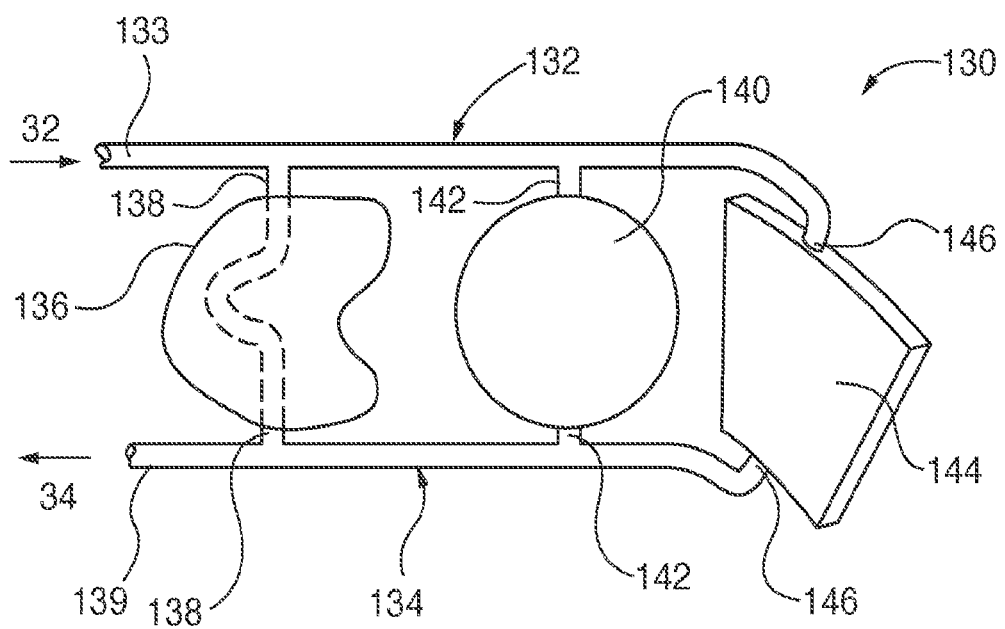
FIG. 12 is a perspective view of a curved, segmented first or second chill plate, with cascading, parallel coolant flow between each sub segment thereof.

FIGS. 11 and 12 are embodiments of segmented chill plates that incorporate plate sub-segments with commonly shared inlets and outlets. Each sub-segment functions as an independent chill plate. Segmented chill plates are useful for packaging and distributing heat absorption and heat isolation capacities into smaller, confined zones within a DEA that cannot physically accommodate a single, larger chill plate having the same heat absorption capacity. They are also useful for conforming to multiple faces of an electronic component, such as a base and one or more lateral sides of a power supply. In other applications, segmented chill plates provide selective heat isolation between components within a DEA housing.

The segmented chill plate 120 incorporates cascading, sequential coolant flow from coolant supply 32 to coolant return 34, via a continuous coolant pipe 122, to each of the respective first 124, second 126 and third 128 chill plate sub-segments. The coolant pipe 122 captured within the chill plate sub-segments has a serpentine profile, similar to the coolant pipe 74 of FIG. 7. In this embodiment of FIG. 11, each of those sub-segments 124, 126, 128 have differing surface area profiles. The coolant inlet side 123 of the coolant pipe 122 is in direct or indirect communication with the coolant supply 32 and the coolant outlet side 129 thereof is in direct or indirect communication with the coolant return 34. Conceptually in some embodiments, the segmented chill plate 120 is readily substituted for any one of the first 52 or second 54 chill plates shown in any of the DEAs of FIG. 2 or 4. For example, if the segmented chill plate 120 is substituted for any one of the second chill plates 54 of FIG. 4, its coolant inlet 123 substitutes for the second coolant inlet 60 and its coolant outlet 129 substitutes for the second coolant outlet 62.

The curved, segmented chill plate 130 of FIG. 12 incorporates parallel coolant flow architecture, with plate coolant-supply manifold 132, whose inlet 133 is in direct or indirect communication with the coolant supply 32, and plate coolant-return manifold 134, whose outlet 135 is in direct or indirect communication with the coolant return 34. In this exemplary coolant flow architecture, a first chill plate sub-segment 136 incorporates a first coolant pipe 138, a second chill plate sub-segment 140 incorporates a second coolant pipe 142 and a third chill plate sub-segment 144 incorporates a third coolant pipe 146. The opposite ends of the first 138, second 140 and third 144 coolant pipes are respectively in fluid communication with the coolant-supply manifold 132 and the coolant-return manifold 134. Each chill plate sub-segment has a different planform profile for conductive heat absorption from a corresponding heat dissipating component within a DEA. The third chill plate sub-segment 144 has a curved planform profile.

The modular, scalable, fluid cooling systems described herein operate within imaging system gantries at lower noise levels than existing forced air, with air-liquid heat exchanger-type cooling systems. In an exemplary modular, fluid cooling system embodiment, designed for incorporation within a long aFOV PET system, such as shown in FIGS. 1 and 10, operating noise within the patient tunnel was measured to be less than fifty-five decibels (55 dB). As shown in FIG. 10, coolant pumps and other noise generating components are in the external cooling apparatus 30 outside the gantry 12. The fluid cooling system embodiments described herein do not need or utilize noisy cooling fans within the gantry 12. Additionally, the acoustic foam liner 16 circumscribing the patient tunnel wall 14 further suppresses noise within the patient tunnel. In contrast, in a comparable long aFOV PET system, employing a forced air-cooling system, the measured noise level in its patient tunnel was on the order greater than ten decibels (>10 dB) higher than that of the exemplary PET system with the modular, fluid cooling system.

Scalable cooling system embodiments disclosed herein maintain thermal operating stability of detector elements, such as SiPMs, no matter how many modular DEAs are ganged together. For example, in a long aFOV PET/CT system, four gantries incorporating the disclosed DEAs are ganged together axially, with the previously described cascading coolant flow between the first chill plates in each DEA, followed by cascading flow through the second chill plates. The cascading cooling flow interconnection reduces the number of coolant fittings and coolant lines within the gantry or gantries. All the interconnected DEAs are desirably serviced by a single coolant pump of the cooling apparatus. The modular DEAs are compact, reducing needed gantry internal volume, despite increasing axial lengths of long aFOV imaging systems.

Although various embodiments have been shown and described in detail herein, others can readily devise many other varied embodiments that still incorporate the claimed invention. The invention is not limited in its application to the exemplary embodiment details of construction and the arrangement of components set forth in the description or illustrated in the drawings. The invention is capable of other embodiments and of being practiced or of being carried out in various ways. In addition, it is to be understood that the phraseology and terminology used herein is for the purpose of description and should not be regarded as limiting. The use of "including", "comprising", or "having", and variations thereof herein is meant to encompass the items listed thereafter and equivalents thereof as well as additional items. Unless specified or limited otherwise, the terms "mounted", "connected" "supported", and "coupled" and variations thereof are to be interpreted broadly; they encompass direct and indirect mountings, connections, supports, and couplings.

What is claimed is:

1. A fluid coolant system for a medical imaging apparatus, comprising:
   a gantry forming a patient tunnel:
   a cooling apparatus, coupled to and external the gantry, having a coolant supply for supplying fluid coolant to the gantry, and a coolant return for returning the fluid coolant to the cooling apparatus;
   a detector electronic assembly (DEA) located within the gantry and is coupled to the cooling apparatus, having:
      a housing:
      detector elements located in the housing and configured to detect incident photons of electromagnetic radiation originating outside of the housing, the detector elements having detector element components projecting away therefrom, defining a first surface profile:
      a printed circuit board and a power supply located in the housing, at least one of which defines a second surface profile;
      a fluid cooled, first chill plate, which is in thermally conductive, direct contact with the detector element components, for cooling the detector element components, wherein the first chill plate includes a first inlet for receiving the fluid coolant from the coolant supply and a first outlet for discharging the fluid coolant to the coolant return; and
      a fluid cooled, second chill plate, which is in thermally conductive, direct contact with at least a portion of the second surface profile of the at least one of the printed circuit board and/or the power supply, for cooling the at least one of the printed circuit board and/or the power supply, wherein the second chill plate includes a second inlet for receiving the fluid coolant from the coolant supply and a second outlet for discharging the fluid coolant to the coolant return;
   wherein the first chill plate defines a first surface profile that is a mirror image of the first surface profile of the detector elements, the respective first surface profiles in thermally conductive, direct contact with each other; and
   wherein, the second chill plate defines a second surface profile that is a mirror image of the second surface profile of the at least one of the printed circuit board and/or the power supply, the respective second surface profiles in thermally conductive, direct contact with each other.

2. A fluid coolant system for a medical imaging apparatus comprising:
   a gantry forming a patient tunnel;
   a cooling apparatus, coupled to and external the gantry, having a coolant supply for supplying fluid coolant to the gantry, and a coolant return for returning the fluid coolant to the cooling apparatus:
   a detector electronic assembly (DEA) located within the gantry and is coupled to the cooling apparatus, having:
      a housing;
      detector elements located in the housing and configured to detect incident photons of electromagnetic radiation originating outside of the housing, the detector elements in the DEA facing the patient tunnel, wherein the detector elements having detector element components projecting radially away from the patient tunnel;
      a printed circuit board and a power supply located in the housing;
      a fluid cooled, first chill plate in thermally conductive, direct contact with at least one of the detector element components and oriented in the housing intermediate the detector element components and the detector elements, for cooling the detector elements, wherein the first chill plate includes a first inlet for receiving the fluid coolant from the coolant supply and a first outlet for discharging the fluid coolant to the coolant return; and
      a fluid cooled, second chill plate in thermally conductive, direct contact with at least one of the printed circuit board and/or the power supply for cooling the at least one of the printed circuit board and/or the power supply, wherein the second chill plate includes a second inlet for receiving the fluid coolant from the coolant supply and a second outlet for discharging the fluid coolant to the coolant return;
   wherein the first outlet of the first chill plate is in fluid communication with the second inlet of the second chill plate, so that fluid coolant from the coolant supply first flows through the first chill plate and flows through the second chill plate sequentially.

3. The fluid coolant system of claim 2, wherein the second chill plate has a first side and a second side that is opposed to the first side, wherein the printed circuit board and the power supply are thermally coupled to the respective first and second sides of the second chill plate.

4. A detector electronic assembly (DEA) for a medical imaging apparatus, comprising:
a housing;
detector elements retained in the housing and configured to detect incident photons of electromagnetic radiation originating outside of the housing, the detector elements having detector element components projecting away therefrom, defining a first surface profile;
a printed circuit board and a power supply located in the housing, wherein at least one of which defines a second surface profile;
a fluid cooled, first chill plate, wherein the first chill plate is in thermally conductive, direct contact with at least a portion of the first surface profile of the detector element components, for cooling the detector elements, wherein the first chill plate includes a first inlet for receiving fluid coolant and a first outlet for discharging the fluid coolant; and
a fluid cooled, second chill plate, wherein the second chill plate is in thermally conductive, direct contact with at least a portion of the second surface profile of the at least one of the printed circuit board and/or the power supply, for cooling the at least one of the printed circuit board and/or the power supply, wherein the second chill plate includes a second inlet for receiving the fluid coolant and a second outlet for discharging the fluid coolant;
the respective first and second inlets and outlets accessible outside the housing,
wherein, the first chill plate defines a first surface profile that is a mirror image of the first surface profile of the detector elements, and wherein the first surface profiles are in thermally conductive, direct contact with each other; and
wherein, the second chill plate defines a second surface profile that is a mirror image of the second surface profile of the at least one of the printed circuit board and/or the power supply, and wherein the respective second surface profiles are in thermally conductive, direct contact with each other.

5. The DEA of claim 4, wherein the first outlet of the first chill plate is in fluid communication with the second inlet of the second chill plate, so that the fluid coolant from the coolant supply first flows through the first chill plate and flows through the second chill plate sequentially.

6. A detector electronic assembly (DEA) for a medical imaging apparatus comprising:
a housing:
detector elements retained in the housing and configured to detect incident photons of electromagnetic radiation originating outside of the housing;
a printed circuit board and a power supply located in the housing:
a fluid cooled, first chill plate thermally conductively coupled to the detector elements, for cooling the detector elements, wherein the first chill plate includes a first inlet for receiving fluid coolant and a first outlet for discharging the fluid coolant; and
a fluid cooled, second chill plate thermally conductively coupled to at least one of the printed circuit board and/or the power supply, for cooling the at least one of the printed circuit board and/or the power supply, wherein the second chill plate includes a second inlet for receiving the fluid coolant and a second outlet for discharging the fluid coolant;
the respective first and second inlets and outlets accessible outside the housing;
wherein, the second chill plate has a first side and a second side that is opposed to the first side, and
wherein the printed circuit board and the power supply are thermally coupled to the respective first and second sides of the second chill plate.

7. A detector electronic assembly (DEA) for a medical imaging apparatus, comprising:
a housing:
detector elements retained in the housing and configured to detect incident photons of electromagnetic radiation originating outside of the housing:
a printed circuit board and a power supply located in the housing;
a fluid cooled, first chill plate thermally conductively coupled to the detector elements, for cooling the detector elements, wherein the first chill plate includes a first inlet for receiving fluid coolant and a first outlet for discharging the fluid coolant; and
a fluid cooled, second chill plate thermally conductively coupled to at least one of the printed circuit board and/or the power supply, for cooling the at least one of the printed circuit board and/or the power supply, wherein the second chill plate includes a second inlet for receiving the fluid coolant and a second outlet for discharging the fluid coolant;
the respective first and second inlets and outlets accessible outside the housing;
further comprising a thermally conductive material interposed between the first chill plate and the detector elements and/or between the second chill plate and the at least one of the printed circuit board and/or the power supply.

8. A detector electronic assembly (DEA) for a medical imaging apparatus, comprising:
a housing;
detector elements retained in the housing and configured to detect incident photons of electromagnetic radiation originating outside of the housing;
a printed circuit board and a power supply located in the housing:
a fluid cooled, first chill plate thermally conductively coupled to the detector elements, for cooling the detector elements, wherein the first chill plate includes a first inlet for receiving fluid coolant and a first outlet for discharging the fluid coolant; and
a fluid cooled, second chill plate thermally conductively coupled to at least one of the printed circuit board and/or the power supply, for cooling the at least one of the printed circuit board and/or the power supply, wherein the second chill plate includes a second inlet for receiving the fluid coolant and a second outlet for discharging the fluid coolant;
the respective first and second inlets and outlets accessible outside the housing;
further comprising at least one of the first or the second chill plates respectively having:
a coolant pipe with a first end forming the respective first or second inlet and a second end forming the respective first or second outlet; and
split construction respective top and bottom plates in direct contact with and capturing the coolant pipe therebetween.

9. A method for scalable cooling of a gantry of a medical imaging apparatus, comprising:
providing a gantry forming a patient tunnel;
providing a cooling apparatus, wherein the cooling apparatus is coupled to and is external the gantry, and wherein the cooling apparatus includes a coolant supply for supplying fluid coolant to the gantry, and a coolant return for returning the fluid coolant to the cooling apparatus:
providing a selected plurality of detector electronic assemblies (DEAs) for orientation within the gantry, each respective DEA having:
a housing:
detector elements retained in the housing and configured to detect incident photons of electromagnetic radiation originating outside of the housing:
other electronic components located in the housing, including a printed circuit board and a power supply;
a fluid cooled, first chill plate thermally conductively coupled to the detector elements, for cooling the detector elements and oriented in the housing intermediate the detector elements and the other electronic components, wherein the first chill plate includes a first inlet for receiving the fluid coolant from the coolant supply and a first outlet for discharging the fluid coolant to the coolant return; and
a fluid cooled, second chill plate for cooling the other electronic components, the second chill plate having opposed first and second sides, respectively thermally conductively coupled to the printed circuit board on the first side and to the power supply on the second side, wherein the second chill plate includes a second inlet for receiving the fluid coolant from the coolant supply and a second outlet for discharging the fluid coolant to the coolant return;
the respective first and second inlets and outlets of the first and second chill plates externally accessible outside of each housing;
orienting the plurality of DEAs within the gantry, so that:
each housing is commonly coupled to a housing support of the gantry axially in sequence about an outside of the patient tunnel, parallel to a central axis defined by the patient tunnel; and
each detector element faces the patient tunnel, tangential to a circumference thereof, with components of the detector element projecting radially away from the patient tunnel;
coupling the first inlet of the first chill plate of and the second inlet of the second chill plate of each DEA directly or indirectly to the coolant supply of the cooling apparatus;
coupling the first outlet of the first chill plate and the second outlet of the second chill plate of each DEA directly or indirectly to the coolant return of the cooling apparatus;
scaling cooling capacity of the external cooling apparatus in proportion to a number of the plurality of DEAs within the gantry that are cooled thereby;
circulating the fluid coolant between the gantry and the cooling apparatus at a flow rate that maintains a specified stable temperature bandwidth for all detector elements in the each of the respective DEAs;
collectively coupling all of the first inlets of the first chill plates to the coolant supply of the cooling apparatus; and
collectively coupling all of the second inlets of the second chill plates to the collective first outlets of the first chill plates, so that the fluid coolant from the coolant supply first flows through all of the first chill plates prior flowing through the second chill plates.

10. The method for scalable cooling of the gantry of claim 9, wherein the first chill plate or the second chill plate further comprises plate sub-segments with commonly shared, respective first or second inlets and first or second outlets.

* * * * *